United States Patent
Gugler et al.

(10) Patent No.: US 9,173,741 B2
(45) Date of Patent: Nov. 3, 2015

(54) METHOD FOR PRODUCING AN IMPLANT HAVING AT LEAST ONE BREAK LINE

(75) Inventors: Christian Gugler, Frauenfeld (CH); Daniel Nadler, Hettlingen (CH); Andreas Meyenhofer, Schlattingen (CH); Simon Bodmer, Winterthur (CH)

(73) Assignee: Jossi Holding AG, Islikon (CH)

( * ) Notice: Subject to any disclaimer, the term of this patent is extended or adjusted under 35 U.S.C. 154(b) by 0 days.

(21) Appl. No.: 13/696,015

(22) PCT Filed: May 4, 2011

(86) PCT No.: PCT/EP2011/057096
§ 371 (c)(1),
(2), (4) Date: Nov. 2, 2012

(87) PCT Pub. No.: WO2011/138353
PCT Pub. Date: Nov. 10, 2011

(65) Prior Publication Data
US 2013/0053976 A1 Feb. 28, 2013

(30) Foreign Application Priority Data
May 7, 2010 (EP) .................... 10162347

(51) Int. Cl.
*A61F 2/34* (2006.01)
*B21D 11/08* (2006.01)
*A61F 2/46* (2006.01)
*A61B 17/80* (2006.01)
(Continued)

(52) U.S. Cl.
CPC .............. *A61F 2/34* (2013.01); *A61F 2/4637* (2013.01); *B21D 11/08* (2013.01); *A61B 17/80* (2013.01); *A61F 2/3094* (2013.01); *A61F 2/30744* (2013.01); *A61F 2/32* (2013.01); *A61F 2/38* (2013.01); *A61F 2/40* (2013.01); *A61F 2002/30561* (2013.01); *A61F 2002/30682* (2013.01); *A61F 2002/3401* (2013.01); *A61F 2002/4641* (2013.01); *A61F 2310/00017* (2013.01); *A61F 2310/00023* (2013.01); *A61F 2310/00029* (2013.01); *A61F 2310/00041* (2013.01); *Y10T 29/49995* (2015.01); *Y10T 225/12* (2015.04)

(58) Field of Classification Search
CPC ........ A61F 2/34; B21D 11/08; B21D 11/085; Y10T 29/49995
USPC ............ 29/413, 557, 414; 623/22.34; 72/374, 72/470, 471
See application file for complete search history.

(56) References Cited

U.S. PATENT DOCUMENTS 2,697,953 A * 12/1954 Chapman ........................ 72/356
3,359,773 A * 12/1967 Stuchbery ....................... 72/325
(Continued)

FOREIGN PATENT DOCUMENTS

CN 201432039 3/2010
DE 102008022329 11/2009
(Continued)

*Primary Examiner* — Jermie Cozart
(74) *Attorney, Agent, or Firm* — Davis & Bujold, P.L.L.C.; Michael J. Bujold

(57) ABSTRACT

An implant, having a surface segment with at least one break line delineating an opening or recess of a closure segment which can be removed from the surface segment, is produced by first making a sub-assembly of the implant and then weakening the material in the region of the break line by material deformation.

9 Claims, 6 Drawing Sheets

(51) Int. Cl.
    *A61F 2/30*     (2006.01)
    *A61F 2/32*     (2006.01)
    *A61F 2/38*     (2006.01)
    *A61F 2/40*     (2006.01)

(56) References Cited

U.S. PATENT DOCUMENTS

| | | | | |
|---|---|---|---|---|
| 4,012,935 A | * | 3/1977 | Holk et al. | 72/325 |
| 4,122,791 A | * | 10/1978 | Brown | 83/880 |
| 4,504,181 A | * | 3/1985 | Khoury | 413/17 |
| 5,370,702 A | | 12/1994 | Jones | |
| 5,782,929 A | | 7/1998 | Sederholm | |

FOREIGN PATENT DOCUMENTS

| | | | |
|---|---|---|---|
| EP | 0701420 | | 3/1996 |
| EP | 1338256 | | 8/2003 |
| EP | 1728489 | | 12/2006 |
| FR | 2826865 | | 1/2003 |
| FR | 2838329 | | 10/2003 |
| GB | 1349789 A | * | 4/1970 |
| WO | 2010/023447 | | 3/2010 |

* cited by examiner

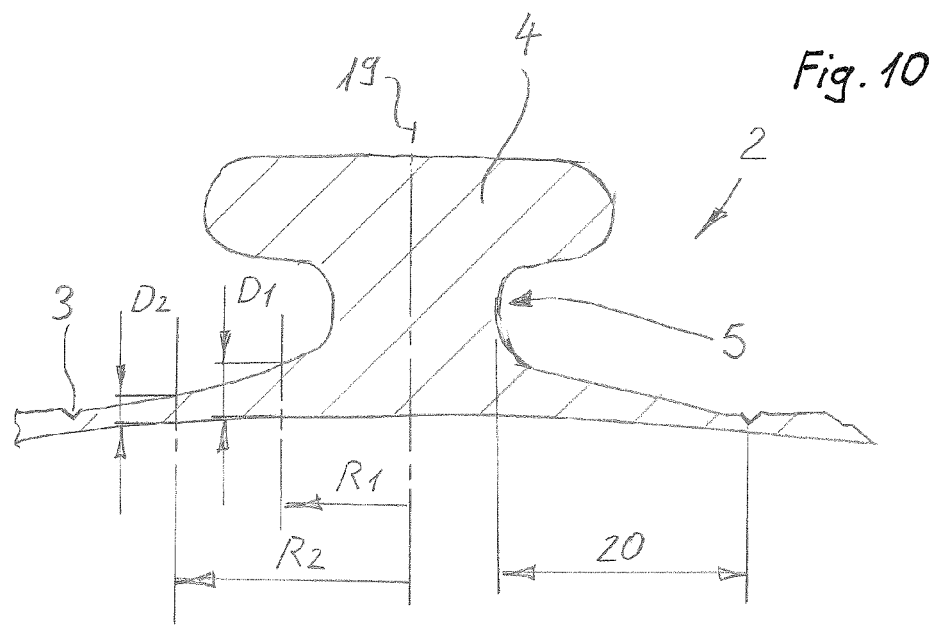
Fig. 10
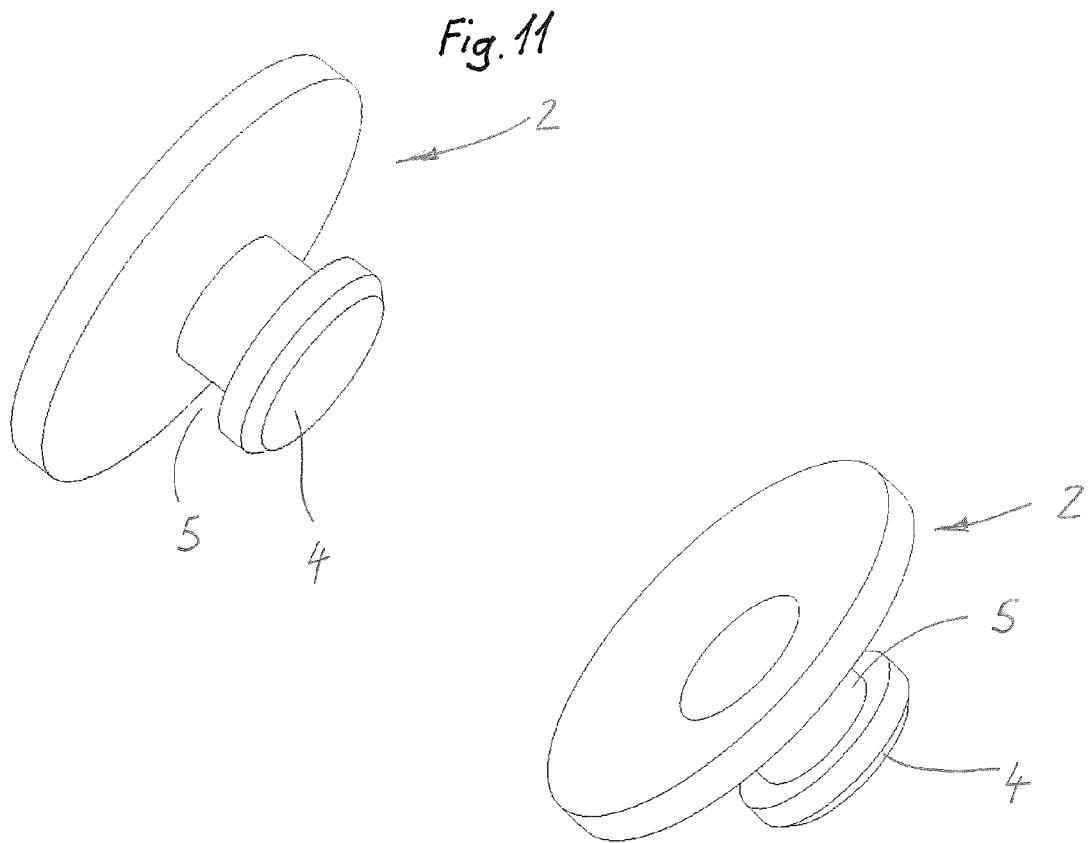
Fig. 11
Fig. 12

METHOD FOR PRODUCING AN IMPLANT HAVING AT LEAST ONE BREAK LINE

BACKGROUND OF THE INVENTION

The present invention relates to a production method for an implant.

In implants, it can be advantageous if, for example, individual screw holes or openings can be selectively opened. This is particularly important in hip joint sockets, since abrasion particles from the joint socket can pass through unused screw holes into the area between implant and bone. However, in osteosynthesis plates, it can also be advantageous to selectively close individual screw openings or to be able to remove certain areas of the implant.

It is therefore proposed in FR 2826865 to produce hip joint sockets in which the screw holes are closed by covers that are secured on the outside of the joint socket by individual weld points. If one of the screw holes is needed, the cover can be removed by breaking these weld points.

U.S. Pat. No. 5,782,929 discloses a hip joint socket made of titanium, in which the screw openings are closed by titanium plugs that have been sintered with the joint socket. The plugs are produced separately from the hip joint socket and are only later fitted into the openings. The plugs are connected to the socket by sintering for several hours in an oven at ca. 1200° C.

A disadvantage of the two methods described is that the production of such joint sockets involves several steps and, as a result, is correspondingly complex. In addition, the strength of the connection of the covers or plugs to the joint socket can be different depending on the opening.

WO 2010/023447 describes a prosthesis made of carbon-fiber-reinforced polyether ether ketone (CFR-PEEK). In one embodiment, the screw openings can be closed by pieces that can be broken out. During production, a predetermined break line is in this case created in the area of the openings by means of targeted reduction of the material thickness. The prosthesis can be produced from one piece by machining or can also be produced by injection molding.

It is known from EP 0 701 420 that hip joint sockets with removable covers that can be broken out can be produced by drilling cylindrical blind holes on the inner face of the socket. The blind holes are formed in such a way that a material thickness of below 0.65 mm remains between the outer face of the joint socket and the end of the hole. In this way, the cover over the blind hole can be broken out when so required.

FR 2 838 329 describes a hip joint socket having screw openings closed by covers that are connected materially to the hip joint socket. The covers are bounded by an area of reduced material thickness, which allows the covers to be easily broken out. Toward the interior of the joint socket, the covers have additional projections, into which further plugs can be fitted.

It is likewise known from U.S. Pat. No. 5,370,702 that removable covers over screw openings can be produced by reduced material thickness. The covers disclosed in this patent have, in the direction of the interior of a hip joint socket, spike-like projections that can be gripped by a suitable tool and that make the covers easier to break out.

EP 1 338 256 describes a hip joint socket with screw openings that can be punched out. The material thickness of the hip joint socket is reduced in the area of these openings in order to make them easier to punch out. This document also describes tools for punching out the screw openings. The area with reduced material thickness can additionally have a circular notch in order to additionally reduce the punching-out force needed for removal.

The stated covers have the principal disadvantage that problems are caused by their production by machining and by the necessary small material thicknesses, since these material thicknesses often lie within the fault tolerance of customary machines in the case of multiple clamping. Moreover, on account of the required precision, their production is laborious and expensive.

SUMMARY OF THE INVENTION

It is now an object of the present invention to make available a method of the type mentioned at the outset that avoids the stated disadvantages and that permits very precise dimensioning of the predetermined break line, without adjacent areas being deformed or being influenced in terms of their dimensional accuracy or otherwise overloaded, e.g. thermally. Moreover, the method is intended to be inexpensive and to be suitable for implants of different design.

In the method according to the invention, a semi-finished implant is produced in a first production process that preferably involves machining. A predetermined break line is then created by deforming the material and reducing the material thickness.

The first method step can be performed by a known production process, for example milling and/or turning. Thereafter, the predetermined break line is then produced. Depending on the design of the implant, it may be advantageous if the wall portions provided for the arrangement of the predetermined break line have been substantially pre-formed by the first production process, for example by arrangement of a depression or similar. It is particularly preferable for at least one blind hole to be formed in the semi-finished implant, with a predetermined break line being impressed on the bottom of said hole in the second method step.

A particularly advantageous aspect of the method according to the invention is the fact that, by deforming the material at the predetermined break line, it is also possible to efficiently achieve very small wall thicknesses. Moreover, a predetermined break line can also be formed on an implant with complex surface geometry. Moreover, the minimal wear of the used embossing dies means that a very high degree of reproducibility can be achieved.

In the method according to the invention, the deforming of the material is preferably performed by forming under pressure in the cold state and also in the hot state. Different embossing dies can be used depending on the geometry that is to be achieved. By varying the embossing pressure and/or the path of movement, the wall thickness can also be varied in the area of the predetermined break line. In the case of high-strength materials, the embossing force can be reduced by hot working, or the degree of forming can be deliberately increased.

In the method according to the invention, the deforming of the material is preferably performed in such a way that the forming forces or the material flow are directed into the closure portion. The embossing die can be of such a nature that the embossing forces, generated by the embossing pressure, and the resulting material flow can be directed into the closure portion. This prevents disruptive deformations occurring on the implant body for example. In addition, this permits the production of predetermined break lines that are very thin, extend in any desired manner and break off with high precision.

The removable closure portion is preferably produced in such a way that at least one engagement means for the attachment of an instrument is formed. This engagement means preferably has the form of a material projection with an undercut. However, the engagement means can also have other forms, for example slits for engagement of a screwdriver, threads or the like. Such an engagement means has the advantage of making it easier for the closure portion to be broken out. Moreover, an engagement means arranged asymmetrically with respect to the predetermined break line permits a reduction of up to 80% in the maximum force needed to remove the closure portion.

The wall thickness in the area of a predetermined break line is reduced preferably to 0.01 mm to 1 mm, particularly preferably to 0.1 mm to 0.3 mm, by the deforming of the material. This wall thickness is sufficient to prevent inadvertent breaking out of the closure portion, while still being thin enough to allow an opening or recess to be exposed under the effect of force and without mechanical assistance. This makes it possible, for example, to remove individual closure portions during the operation, sometimes even with the implant already inserted.

Moreover, the method can preferably be such that, during the deforming of the material, the closure portion is additionally bent convexly. Alternatively, the deforming of the material can also create closure portions that are bent concavely or that have an undulating form. Concave or convex bending of the closure portion can make the latter more easily accessible for removal and can make the removal itself easier.

The wall portion surrounding the predetermined break line can be supported during the deforming of the material. This prevents deformation of the surrounding material by the compressing pressure.

A further object of the present invention is to create an implant comprising a wall portion having at least one predetermined break line.

The implant according to the invention has a wall portion with at least one predetermined break line that is created by means of weakening of the material thickness by deforming the material.

The implant is preferably a joint socket, particularly preferably a hip joint socket. Alternatively, however, the implant can also be designed as a shoulder joint socket, a femoral or humeral shaft implant, a knee prosthesis, an intramedullary nail or an osteosynthesis plate.

The closure portion delimited by the predetermined break line is preferably formed in a circular, oval, elliptic or polygonal shape, or as a combination thereof.

Alternatively, the closure portion can also be formed on the implant in such a way that it is bounded at least partially by an outer edge of the implant. In this way, removable edge areas can be produced on an implant, for example on an osteosynthesis plate.

The implant is preferably made of a metallic material, particularly preferably of titanium, a titanium alloy, a cobalt-chromium alloy, a magnesium alloy or a steel alloy. Alternatively, the implant can also be made of a non-metallic material, e.g. polyether ether ketone (PEEK) or polyoxymethylene (POM).

The closure portion preferably has engagement means for the attachment of an instrument. This engagement means is particularly preferably designed, for example, as a mushroom-shaped material projection with an undercut. This permits simple and safe removal of the closure portion by an instrument.

Further advantages can be achieved if the wall thickness at the closure portion increases in at least one loading portion with increasing distance from the predetermined break line toward the center of the closure element, in such a way that the material cross section perpendicular to the closure portion is always approximately the same size in surface terms at each point of the loading portion. This condition can be met particularly advantageously on a closure portion having a rotationally symmetrical design. With increasing wall thickness toward the center, the radius also decreases, whereby the cylinder surface of the material cross section remains identical at each radius. In the case of very thin closure portions, it is thus possible to prevent uncontrolled tearing-off outside the predetermined break line.

A particularly advantageous device for carrying out the method has two embossing dies designed as female mold and male mold or two embossing dies designed as male mold. In addition, the device can have a support element that supports the wall portion adjacent to the predetermined break point. The prevents the occurrence of unwanted deformations outside the predetermined break line and permits exact positioning of the semi-finished implant in the device.

The removal of the closure portion is advantageously performed using a suitable instrument. For example, the instrument has an elongate handle and engagement means. The engagement means can be connected releasably to the closure portion.

The elongate handle can be used to apply a force for removing the closure portion from the wall of the implant. The engagement means are used to transfer the force from the handle to the closure portion, and the closure portion can thus be removed safely and easily from the implant wall.

The engagement means are preferably designed in such a way that they can be connected to an engagement means arranged on the closure portion. In this way, the closure portion can be connected securely to the instrument, which also permits removal of a closure portion when the implant is already inserted.

A closure portion according to the invention can also be removed by being subjected to pressure forces or tensile forces. This can be performed, for example, by pressing or striking and by pulling. Alternatively, a closure portion according to the invention can also be removed by bending or turning forces.

BRIEF DESCRIPTION OF THE DRAWINGS

Further advantages and individual features of the invention will become clear from the following description of illustrative embodiments and from the drawings, in which:

FIG. 10 shows a greatly enlarged cross section through a further closure portion with an undercut, FIG. 11 shows a perspective view of a further closure portion, FIG. 12 shows the closure portion according to FIG. 11 from another perspective.

DETAILED DESCRIPTION OF THE INVENTION

Figure 1:
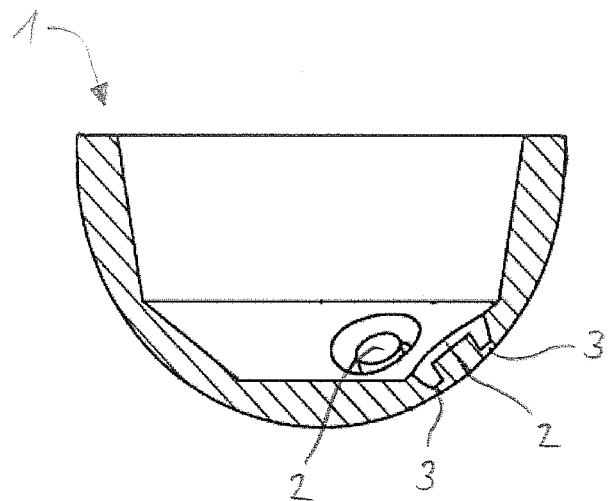
FIG. 1 shows a schematic cross section through an implant according to the invention.

FIG. 1 is a schematic cross section of an implant 1 in which closure portions 2 delimited by predetermined break lines 3 have been formed by the method according to the invention. The implant 1 is configured by way of example as a hip joint socket. Alternatively, however, the implant can also be another implant, for example an osteosynthesis plate. The implant 1 has, for example, two closure portions 2. However, an implant 1 can also have only one closure portion 2 or more than two closure portions 2. The closure portions 2 can be arranged in any desired arrangement on the surface of the implant 1.

Figure 2:
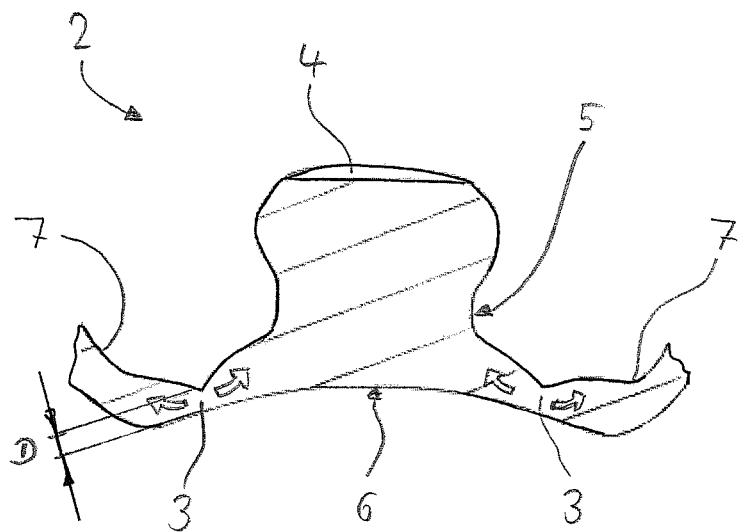
FIG. 2 shows a cross section through a closure portion with predetermined break line, in a greatly enlarged view.

FIG. 2 shows a schematic section through a closure portion of an implant, in which a closure portion 2 delimited by a predetermined break line 3 has been formed using the method according to the invention. Compared to the surrounding wall portion 7, the predetermined break line 3 has a smaller material thickness D. The material thickness D is typically less than 1 mm. The material flow obtained by the shaping process, indicated by way of example by arrows, is preferably directed specifically into the closure portion 2. Alternatively, however, the material flow can also be directed specifically into the surrounding wall portion. The closure portion 2 has an engagement means 4 which, in this example, is designed as a material projection with undercut 5. Alternatively, the engagement means 4 can also have other shapes. The closure portion 2 additionally has a concave arch 6. Alternatively, the arch 6 can also be convex or undulating. Alternatively, the closure portion 2 can also be flat.

Figure 3A:
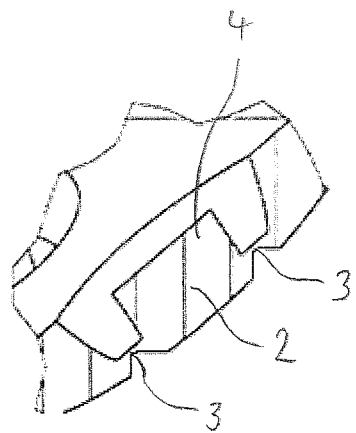
FIGS. 3a-3e show five different schematic cross sections through removable closure portions with predetermined break lines.
Figure 3B:
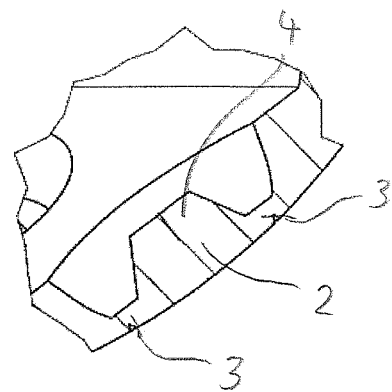
Figure 3C:
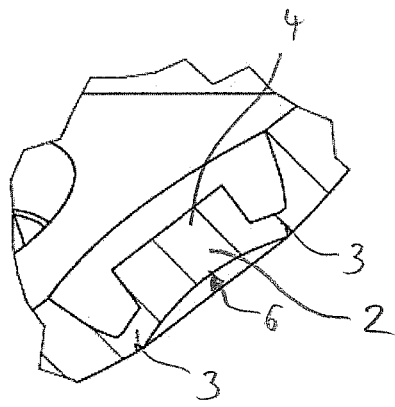
Figure 3D:
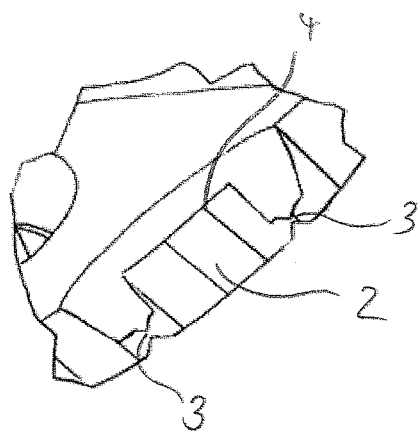
Figure 3E:
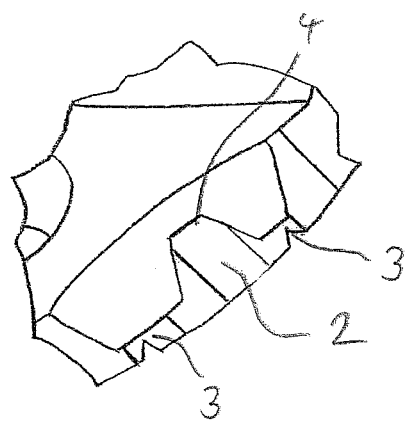

FIGS. 3a to 3e show different embodiments of closure portions 2 of an implant according to the invention. The embodiment in FIG. 3a has an engagement means 4 with a cylindrical or prismatic configuration. FIG. 3b shows an embodiment with a frustoconical engagement means 4. In this embodiment, the predetermined break line 3, which delimits the closure portion 2, has a greater material thickness than the embodiment in FIG. 3a. Another variant is shown in FIG. 3c. In this variant, the outside of the closure portion 4 has a convex arch 6. The closure portion 2 shown in FIG. 3a can be an intermediate step in the production of the closure portion 2 in FIG. 3c. FIG. 3d shows another embodiment of a closure portion 2 in which the material thickness of the predetermined break line 3 has been reduced on both sides of the wall of the implant. FIG. 3e shows another embodiment of a closure portion 3. In this embodiment, the engagement means 4 is not arranged centrally and symmetrically on the closure portion 2, but eccentrically. The individual features of the described embodiments of the closure portion 2 can be combined with one another as required. Different embodiments of a closure portion 2 can also be present on the same implant.

Figure 4:
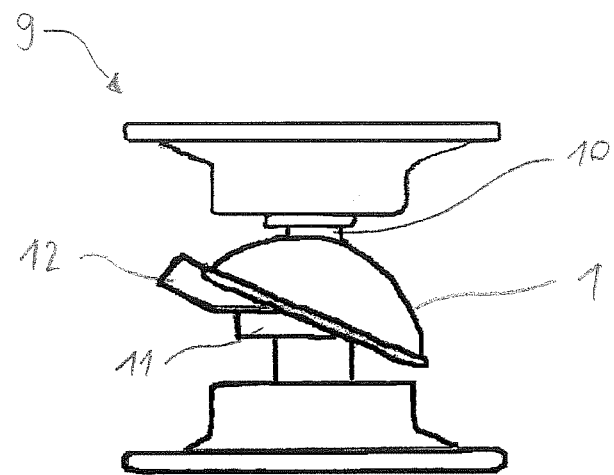
FIG. 4 shows a schematic view of a device for producing an implant, FIGS. 5a/5b show schematic views of the shaping process of the method according to the invention.

FIG. 4 shows a device 9 for producing an implant 1. The implant 1 is clamped between the two dies 10, 11. Support element 12 additionally supports the implant 1.

Figure 5A:
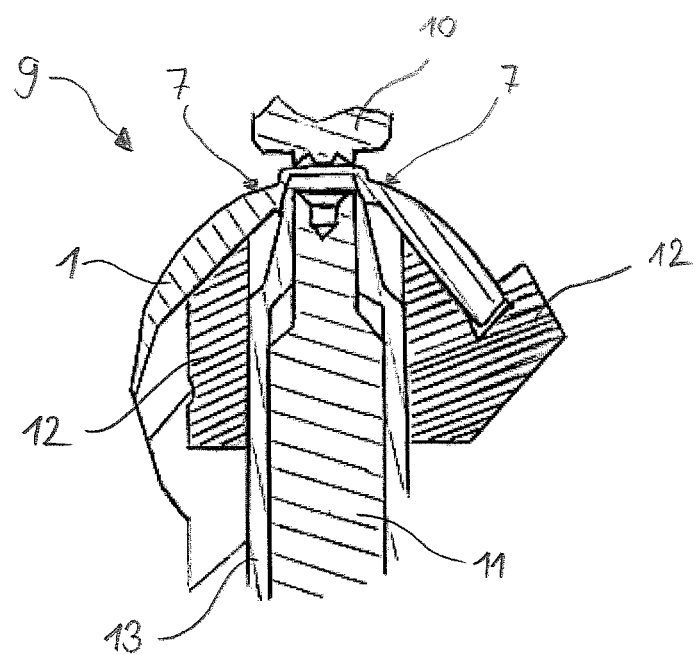
Figure 5B:
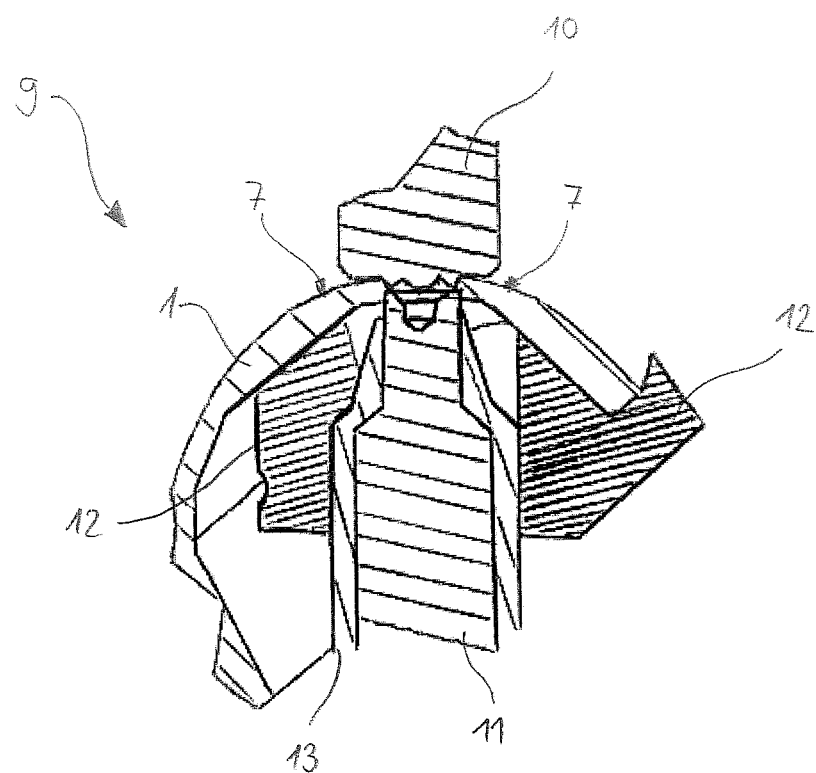

FIGS. 5a and 5b show an illustrative embodiment of the method according to the invention on the basis of a sectional view through a device. The situation before the deforming of the material can be seen in FIG. 5a. The semi-finished implant 1, produced by a first production method, is clamped into the device 9 between the dies 10, 11. The implant 1 is additionally supported by the support element 12. The correct orientation of the implant 1 with respect to the dies 10, 11 is obtained using the guide element 13. FIG. 5b shows the device 9 and the implant 1 during the deforming of the material. The two dies 10, 11 are pressed against each other. The support elements 12, 13 support the wall portion 7 surrounding the predetermined break line.

Figure 6:
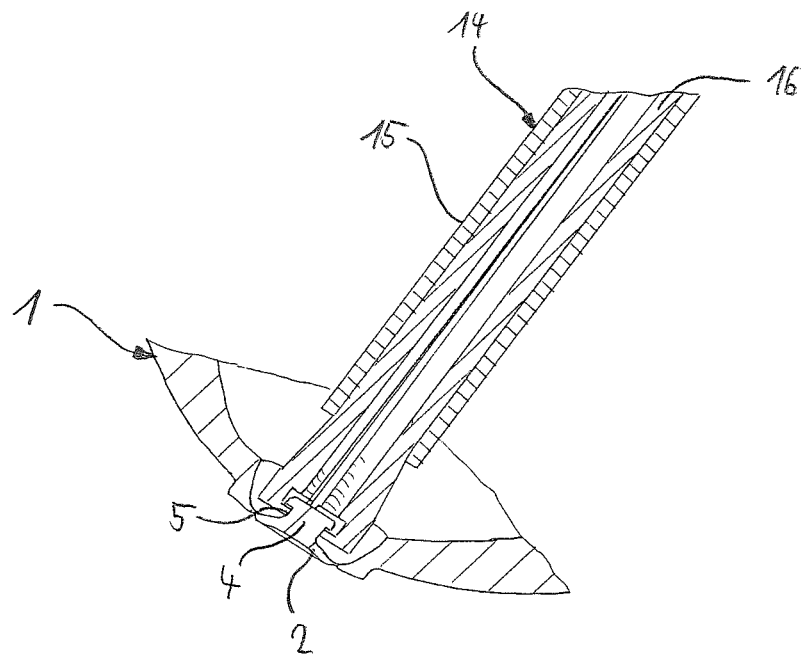
FIG. 6 shows a partial cross section through an implant with an attached instrument for breaking out a closure portion according to the invention.

FIG. 6 shows a sectional view of an instrument 14, which is connected releasably to a closure portion 2. The instrument 14 comprises an elongate handle 15 and engagement means 16. In the embodiment of the instrument 14 shown here, the engagement means 16 are composed of an elongate hollow body with at least the same cross section as the engagement means 4. The handle 15, at least in the area of engagement means 16, is likewise designed as a hollow body that is arranged movably over the engagement means 16. In the example shown, the handle 15 is divided into three parts in this area, which parts are separated from one another by tapering slits. By pushing the handle 15 over the engagement means 16, the cross section thereof narrows or the three parts are pressed concentrically toward one another. In this way, the engagement means 16 can engage on the engagement means 4. The engagement means 16 preferably has additional means that are able to engage in the undercut 5 of the engagement means 4.

Figure 7:
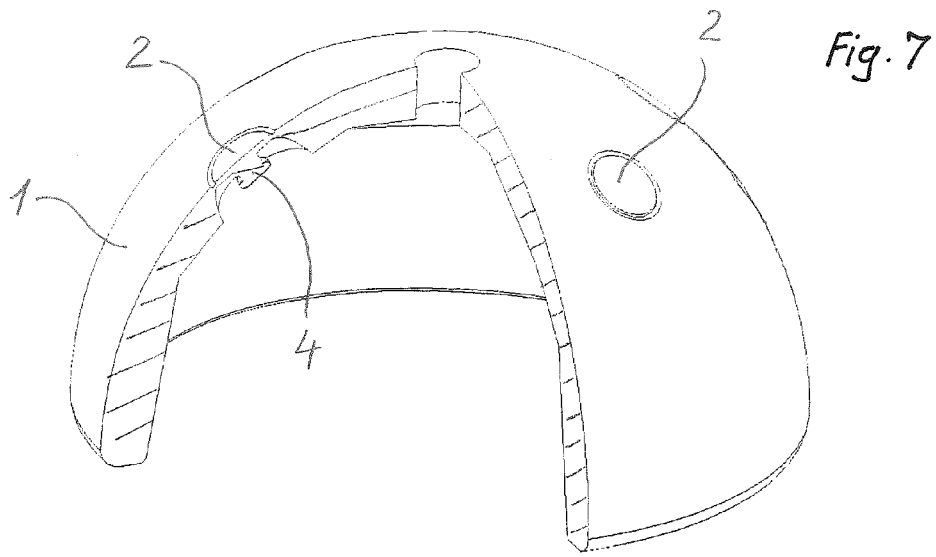
FIG. 7 shows an alternative illustrative embodiment in a perspective view and partially sectioned.
Figure 8:
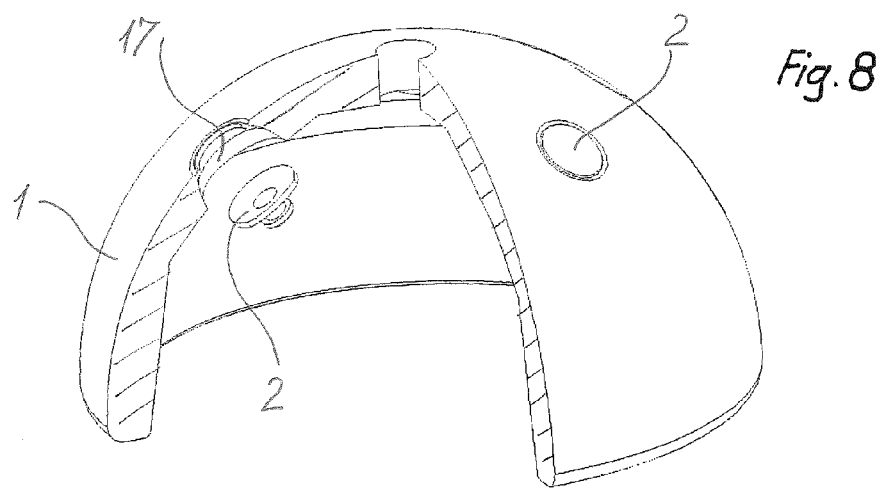
FIG. 8 shows the implant according to FIG. 7 with a closure portion broken out.
Figure 9:
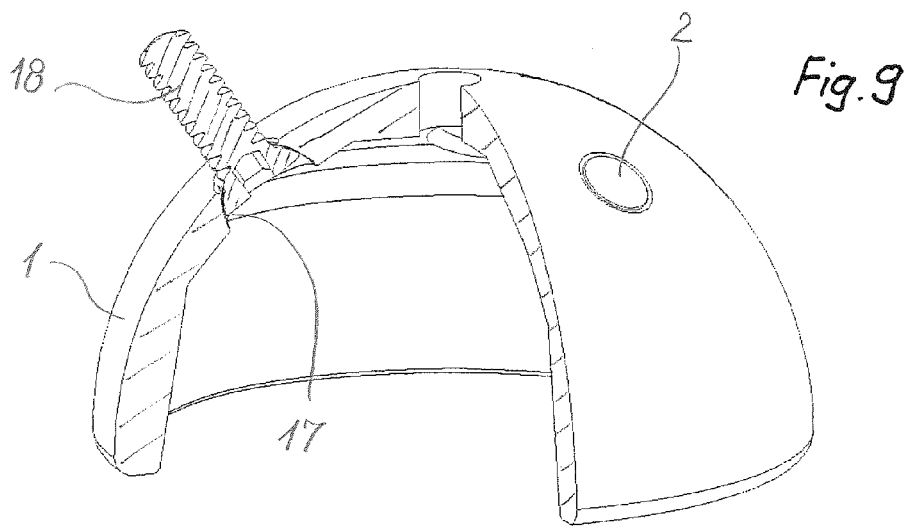
FIG. 9 shows the implant according to FIG. 8 with a screw inserted into the freed opening.

FIGS. 7 to 9 show, once again schematically, the process by which a screw opening on an implant 1 in the form of a hip joint socket is exposed. The outer face of the shell can have any desired surface structure in order to ensure better anchoring in the bone. After a closure portion 2 has been broken off, if appropriate with the hip joint socket already fitted in place, an opening is exposed that forms a screw funnel 17. A screw 18 is inserted into this screw funnel, the head of the screw having a design matching the screw funnel 17.

FIG. 10 shows a closure portion 2 with engagement means 4 that are mushroom-shaped in cross section. The material thickness D increases continuously, in the area of a loading portion 20, from the predetermined break line 3 toward the central axis 19. The loading portion corresponds approximately to the circular ring between the predetermined break line 3 and the smallest diameter at the undercut 5. The material cross section around the central axis 19 is the same in surface terms at the radius R1 as at the radius R2. This derives from the equation $2 \times R1 \times \pi \times D1 = 2 \times R2 \times \pi \times D2$. This configuration ensures that, when the closure portion 2 is engaged, the material breaks at the predetermined break point 3 and not in an uncontrolled manner somewhere in the loading portion 20.

FIGS. 11 and 12 show a further illustrative embodiment of a closure portion 2, which has already been broken out here. The engagement means 4 is approximately cylindrical and has a bevel at the upper edge. The undercut 5 is also cylindrical.

The invention claimed is:

1. A method for producing a hip joint socket implant, comprising at least one wall portion having at least one predetermined circular break line which delimits a closure portion that can be removed from the wall portion under the effect of force in order to expose an opening, said method comprising steps of:

producing a semi-finished implant in a production process, wherein the production process involves machining, whereby the predetermined break line is substantially preformed by said first production process, then clamping the semi-finished implant in a device between two dies, whereby the implant is supported by a support element, and the correct orientation of the implant with respect to said dies is obtained using a guide element which supports the wall portion surrounding the predetermined break line, and finally creating the predetermined break line, whereby the two dies are pressed against each other thereby reducing the wall thickness in the wall portion by deforming the material in the area of the predetermined break line under pressure in a cold or hot state.

2. The method as claimed in claim 1 wherein the deforming of the material is performed in such a way that forming forces or material flow are specifically directed into the closure portion or the implant.

3. The method as claimed in claim 1 wherein the removable closure portion is produced in such a way that at least one engagement means is formed for the attachment of an instrument.

4. The method as claimed in claim 3 wherein the at least one engagement means is a material projection with an undercut.

5. The method as claimed in claim 1 wherein the wall thickness in the area of the predetermined break line is reduced to 0.01 mm to 1 mm.

6. The method as claimed in claim 1 wherein during the deforming of the material the closure portion is additionally bent convexly or concavely or into an undulating form or into a straight form.

7. The method as claimed in claim 1 wherein the implant is made of titanium, a titanium alloy, a cobalt chromium alloy and/or a steal alloy.

8. A method for producing an implant comprising at least one wall portion having at least one predetermined break line which delimits a closure portion that can be removed from the wall portion under the effect of force in order to expose an opening or recess, said method comprising steps of:

producing a semi-finished implant in a production process, then clamping the semi-finished implant in a device between two dies, whereby the implant is supported by a support element, and the correct orientation of the implant with respect to said dies is obtained using a guide element which supports the wall portion surrounding the predetermined break line, and then creating the predetermined break line by reducing the wall thickness in the wall portion by deforming the material in the area of the predetermined break line, wherein during the deforming of the material, the closure portion is additionally bent concavely.

9. A method for producing an implant comprising at least one wall portion having at least one predetermined break line which delimits a closure portion that can be removed from the wall portion under the effect of force in order to expose an opening or recess, said method comprising steps of:

producing a semi-finished implant in a production process, then clamping the semi-finished implant in a device between two dies, whereby the implant is supported by a support element, and the correct orientation of the implant with respect to said dies is obtained using a guide element which supports the wall portion surrounding the predetermined break line, and then creating the predetermined break line by reducing the wall thickness in the wall portion by deforming the material in the area of the predetermined break line, wherein the removable closure portion is produced in such a way that at least one engagement means is formed for the attachment of an instrument, wherein the at least one engagement means is a material projection with an undercut.

* * * * *